United States Patent [19]

Girardon et al.

[11] Patent Number: 4,503,036

[45] Date of Patent: Mar. 5, 1985

[54] PROCESS FOR PRODUCING A BIOCHEMICAL VACCINE AGAINST SALMONELLA INFECTION

[75] Inventors: Philippe Girardon; Jean Amen, both of Versailles, France

[73] Assignee: L'Air Liquide, Societe Anonyme Pour l'Etude et l'Exploitation des Procedes Georges Claude, Paris, France

[21] Appl. No.: 447,503

[22] Filed: Dec. 7, 1982

[30] Foreign Application Priority Data

Dec. 10, 1981 [FR] France ............................. 81 23067

[51] Int. Cl.³ ................... A61K 39/112; C12P 21/00
[52] U.S. Cl. ................................... 424/92; 435/68; 435/253
[58] Field of Search ............... 424/92, 88; 435/68, 435/253

[56] References Cited

PUBLICATIONS

Chemical Abstracts, vol. 83, p. 312, Abstract No. 33019e, 1975.
Chemical Abstracts, vol. 95, Abstract No. 201784u, 1981.
Biological Abstracts, vol. 63, Mar. 15, 1977, #33776, p. 3317, E. J. Johnson, Anatomical Locus of the Common Enterobacterial Antigen.
Biol. Abstr., vol. 66 No. 4, p. 2186, #22334, Mamay et al., Outer Membrane Proteins Antigens in an Enzyme-linked Immunosorbent Assay . . . .
Chem. Abstracts, vol. 91, No. 25, 12-17-79, p. 501, No. 209139a Svenson et al., Artificial Salmonella Vaccines O-Antigenic Oligo-Saccharide . . . .
Biol. Abstracts, vol. 69, No. 2, 1980, p. 1023 Ref. #9632 #9624, Kuusi et al. Immununization with Major Outer Membrane Proteins in Experimental . . . .
Biol. Abstr., vol. 73, No. 6, 1982, Ref. 39195, Res. No. 39201, Kuusi et al., Immunization with Major Outer Membrane Protein (Porin) Preparations in Experimental . . . .
Chem. Abstracts, vol. 96, No. 5, Feb. 1, 1982, p. 313 #31280c, Tufano et al., Receptorial and Antigenic Properties of Precursor Proteins to 34K and 36K Porins . . . .

*Primary Examiner*—Blondel Hazel
*Attorney, Agent, or Firm*—Browdy and Neimark

[57] ABSTRACT

A bacterial vaccine against Salmonella fevers, typhoid and paratyphoid fevers is obtained by fermentation, extraction and purification, vaccinating membrane antigens being extracted by putting the bacterial residue, obtained by centrifuging, in contact with a solvent of the tris (hydroxyalkyl) aminoalkane class, with stirring, at lowered temperature, pH adjusted between 8.4 and 8.6 for a period of at least some 60 hours, then, separated by decanting, followed by purifying the antigens and fractionating by ultrafiltration, and then freeze-drying the vaccinating antigen fraction. Such vaccinating antigen fraction has a molecular weight greater than 50,000, preferably 300,000, and is used to vaccinate humans and animals.

11 Claims, No Drawings

PROCESS FOR PRODUCING A BIOCHEMICAL VACCINE AGAINST SALMONELLA INFECTION

FIELD OF INVENTION

This invention relates to obtaining a biochemical vaccine against Salmonella fevers, typhoid and paratyphoid fevers.

BACKGROUND

The threat of an epidemic of Salmonella fevers is constant in the world as shown by epidemiological reports and the seriousness of the spread of epidemics due to various Salmonellas which have evolved to have an increased resistance to antibiotics.

It has been known for a long time that there is no parallelism between the proportion of anti-O, anti-H or anti Vi agglutinant antibodies, shown in the case of Salmonellosis, and the degree of acquired immunity to these bacteria. The only valid criterion of vaccinal effectiveness is the protection of the individual or animal from a similar infectious bacterium.

Several types of vaccines have already been proposed; however, these vaccines exhibit various drawbacks and dangers. Thus, injectable inactive vaccines (TAB) are not without danger for persons who receive them for a relative effectiveness in relation to a test dose not exceeding $10^5$ pathogenic bacteria. On the other hand, oral vaccines, and more particularly those that contain live bacteria, prove more effective but their use still poses a certain number of problems of a practical order inherent in the difficulties of preservation and of a psychological order.

It has been considered that the use of protective purified fractions extracted from bacteria would satisfactorily solve the problem of vaccination against Salmonellas. And knowing that all bacteria can be considered as made up of antigen mosaics, the outside membrane of the ectoplasmatic wall appearing, in Salmonellas (gram negative) as the anatomic support of the vaccinating antigent, an effort was made to find a means of preferential extraction of this vaccinating antigen.

Various works, particularly those of O. Westphal et al of the Max Planck Institute, published particularly in Zentralbl. Bacteriol; Mikrobiol. Hyg. 1 ABt Orig. a. med. mikrobiol. infektionskr. Parasitol 248 (1), 1980, 64-80, showed the use of guanidine thiocyanate, urea and veronal buffer in the extraction of molecules with a protein base, in particular from gram negative bacteria such as *Salmonella typhimurium* and *S. minnesota* and mutant forms 5 R.

SUMMARY OF DESCRIPTION

In a technique of fermentation, extraction and purification, a process has been developed that makes it possible to obtain an active biochemical vaccine against Salmonella fevers affecting humans and animals, as effective as live vaccine, easy to preserve with a long life and easy to administer by injection or orally.

The process of the invention is characterized by a sequence of the following preparatory phases.

In a first stage, fermentation is performed in a suitable liquid medium of an avirulent strain, such as *Salmonella typhimurium* M 206. It is advantageous to keep the temperature of the fermentation medium close tolerance conditions between 33° and 35° C., the temperature of 34° C. being particularly suited to development of *Salmonella typhimurium*. The fermentation is conducted in average aerobiosis for a period that is a functin of the size of the inoculum, the pH of the medium being adjusted to a little above neutrality.

Centrifuging is performed at a slow speed to separate the liquid and bacteria in the form of a bacterial residue which is washed.

Then the membrane antigens are extracted by a determined selective solvent and under precise pH conditions and period. Extraction of the vaccinating membrane antigens is performed by putting the bacterial residue in contact with a solvent of the lower tris (hydroxyalkyl) aminoalkane class. Tris (hydroxymethyl) aminoethane is particularly suited to extraction of membrane antigens within the process.

The solvent is used in a weak concentration and the extraction medium is buffered, the pH being adjusted between 8.4 and 8.6 with a strong acid. Extraction is performed on the bacterial residue with constant stirring, at a lowered temperature, to avoid any enzymatic or microbial development, preferably between 0° and +4° C. The period of extraction of the antigens, with stirring, from the bacterial residue in contact with the buffer-solvent medium is at least some 60 hours, preferably on the order of 70 hours.

Then there are performed decanting by slight centrifuging, and purification and fractionating by ultrafiltration of the surnatant on membranes having different cutting thresholds going from 10,000 to 300,000 to obtain different fractions of the desired molecular weight. Dialysis of the fraction having the lower molecular weight is performed to eliminate salts.

Finally, the vaccinating antigen fraction is freeze-dried by known techniques.

According to an advantageous variant, extraction of the antigens can be performed by a solvent in the presence of a surfactant, such as surfactants in the series of polyoxyethylenes and polyoxyethanols used in a proportion of a few percentages in relation to the extraction medium, preferably on the order of 1%. As surfactants suitable for improving extraction of the vaccinating antigens there can be mentioned polyoxyethylenesorbates sold under the trademark TWEEN, polyoxyethylenelaurylesters sold under the tradename BRIDJ and polyethoxyethanol known under the trademark TRITON. Use of a surfactant is beneficial from the viewpoint of activity; however, it should be noted that the use of a surfactant during extraction can lead to some difficulties in later purification, if the production aims at a purified antigen. In this case, the extract of the vaccinating membrane antigens after purification and fractionating by ultrafiltration is subjected to a thorough purification by an analytic method, such as isoelectric focusing, or on the industrial level on ion exchange resins.

The freeze-dried biochemical vaccines obtained according to the invention, of which the molecular weight of the vaccinating antigen fraction is greater than 50,000, can be used in vaccinating humans and animals, and they vaccinate mice as effectively as live vaccine. Vaccines, of which the molecular weight of the antigen fraction is greater than 300,000, are very advantageous to use for treating Salmonella, typhoid and paratyphoid fevers, because this type of vaccine can be considered for Salmonella Typhi. These vaccines can be prescribed for injection or oral administration. Because they are produced in freeze-dried form, they can be kept for a very long period.

DETAILED EXEMPLARY EMBODIMENTS

The following examples illustrate the invention in a nonlimiting way.

EXAMPLE 1

Fermentation of *Salmonella typhimurium* M 206 was performed in a fermenter having 15 liter useful volume in a eugonic broth type medium with a composition per 1 liter:

| | |
|---|---|
| tryptone | 15 g |
| soya papain peptone | 5 g |
| glucose | 5 g |
| NaCl | 4 g |
| L. cystine | 0.3 g |
| sodium sulfite | 0.2 g |
| sodium citrate | 1 g |

The culture was performed at a temperature of 34° C., with an aeration of 0.5 VVM, the pH was adjusted to 7.7, a slight acidification was observed at the start. The fermentation period was 24 hours. Centrifuging was performed at slow speed, the residue was washed with water, demineralized and weighed.

Extraction was performed on 30 g of bacterial residue (wet weight) with the solvent-buffer tris (hydroxymethyl) aminomethane (0.05M), HCl at 8.5 (200 ml), at a temperature of +4° C., with constant stirring, and at a pH adjusted to 8.5. The extraction yield controlled by absorption at 206 namometers was maximum at the end of an average period of 67 to 72 hours. Beyond that point, a plateau without improvement of extraction yield was observed.

The medium was subjected to a decanting by very light centrifuging, then to an ultrafiltration on membranes with cutting thresholds of 50,000 to 10,000 daltons.

The following fractions were obtained:

| antigen fractions | weight |
|---|---|
| MW > 50,000 | 0.596 g |
| 10,000 < MW < 50,000 | 0.039 g |
| MW < 10,000 | 0.77 g |

Three batches of 100 mice each were vaccinated orally with 200 μg/day for 5 days with each of the three separate fractions.

After 2 weeks, a trial dose of $4.6 \times 10^4$ *Salmonella typhimurium* $C_5$ per mouse was administered. Also a batch of 100 mice were vaccinated with live vaccine Stm Ra and one batch of 100 mice were not vaccinated.

| | Percentage of survival of mice at the end of: | | Relative effectiveness index | |
|---|---|---|---|---|
| Antigen fractions | 12 days | 23 days | 12 days | 23 days |
| MW > 50,000 | 88 | 72 | 0.9 | 0.77 |
| 10,000 < MW < 50,000 | 75 | 54 | 0.65 | 0.42 |
| MW < 10,000 | 45 | 33 | 0.09 | 0.01 |
| Stm Ra live vaccine | 93 | 83 | | |
| Unvaccinated control animals | 40 | 32 | | |

The effectiveness index takes into consideration the percentage of survival and the average period of survival, all in reference to a control.

The antigen fraction having a molecular weight greater than 50,000 daltons, in practice, vaccinated mice as effectively as live vaccine.

EXAMPLE 2

Fermentation and extraction were performed under the same conditions as in Example 1, then the extraction juice was submitted to a light centrifuging, then to an ultrafiltration on membranes having cutting thresholds of 50,000, 100,000 and 300,000 daltons.

Mice were vaccinated orally with 200 μg per day for 5 days with each fo the fractions obtained. The test dose was $5 \times 10^4$ typhimurium $C_5$ per mouse.

The following results were obtained:

| | Percentage of survival of mice at the end of: | | Relative effectiveness index | |
|---|---|---|---|---|
| Antigen fractions | 12 days | 23 days | 12 days | 23 days |
| MW > 300,000 | 30 | 30 | 0.7 | 0.7 |
| 100,000 < MW < 300,000 | 5 | 5 | 0.08 | 0.08 |
| 10,000 < MW < 100,000 | 15 | 10 | 0.3 | 0.18 |
| Smt Ra | 38 | 38 | | |
| Unvaccinated control animals | 0 | 0 | | |

EXAMPLE 3

The fermentation, extraction and ultrafiltration were identical with the above conditions. The antigen fraction having a molecular weight greater than 300,000 underwent an isoelectric focusing making it possible to obtain different fractions assumed to be of a different protein nature with different isoelectric points. Of all the fractions obtained, one of them corresponding to an isoelectric point between 5.5 and 6 vaccinated mice against *Salmonella typhymurium* $C_5$ as effectively as live vaccine.

| | Percentage of survival of mice at the end of: | | Relative effectiveness index | |
|---|---|---|---|---|
| Antigent fractions | 12 days | 23 days | 12 days | 23 days |
| Phi 5.6–6 } MW > 300,000 | 50 | 20 | 0.95 | 0.45 |
| SmT Ra | 52 | 44 | | |
| Unvaccinated control animals | 5 | 0 | | |

The foregoing description of the specific embodiments will solely reveal the general nature of the invention that others can by applying current knowledge, ratherly modify and/or adapt for various applications such specific embodiments without departing from the generic concept, and, therefore, such adaptations and modifications should and are intended to be comprehended within the meaning and range of equivalents of the disclosed embodiments. It is to be understood that the phrasiology of terminology employed herein is for the purpose of description and not of limitation.

What is claimed is:

1. Process for producing a bacterial vaccine for use against Salmonella infections comprising the following preparatory sequence:

fermentation in a suitable liquid medium of an avirulent strain of *Salmonella typhimurium* at a pH slightly above neutrality, in average aerobiosis, at a temperature between 33° and 35° C., for a period that is a function of the amount of inoculum;

centrifuging at a low speed, separation of the bacterial residue;

extraction of a vaccinating antigen fraction of molecular weight greater than 50,000 by putting the bacterial residue in contact with a weak solution of a solvent of the lower tris (hydroxyalkyl) aminoalkane class, with substantially constant stirring, at a temperature of about 0° to 4° C., pH adjusted between 8.4 and 8.6 for a period of at least about 60 hours;

decanting by very slight centrifuging, purification and fractionating of vaccinating antigens by ultrafiltration on membranes having cutting thresholds selected as a function of the desired molecular weights; dialysis of the fraction with the lower molecular weight;

freeze-drying of the vaccinating antigen fraction.

2. Process for producing a bacterial vaccine against Salmonella fevers, as in claim 1, wherein the extractive solvent of the membrane antigens is tris (hydroxymethyl) aminoethane.

3. Process for producing a bacterial vaccine against Salmonella fevers, as in claim 2, wherein the extraction of the vaccinating membrane antigen is performed with constant stirring with adjustment of the pH between 8.4 and 8.6 with a strong acid.

4. Process for producing a bacterial vaccine against Salmonella fever, as in claim 1, wherein extraction of the vaccinating membrane antigens is performed in the presence of a surfactant of the class of polyoxyethylenes and polyoxyethanes in a weak concentration on the order of at most about 1% in relation to the extraction medium.

5. Process for producing a bacterial vaccine against Salmonella fevers as in claim 1, wherein the extract of the vaccinating membrane antigens after purification and fractionality by ultrafiltration is subjected to a thorough purification by isoelectric focusing.

6. Freeze-dried bacterial vaccine that can be used against Salmonella, obtained by the process of claim 5, wherein the molecular weight of the vaccinating antigen fraction is greater than 300,000.

7. A method of vaccination of humans or animals comprising administering to said humans or animals an amount sufficient to protect said humans or animals against typhoid and paratyphoid fevers of the freeze dried bacterial vaccine of claim 6 to protect said humans or animals against typhoid and paratyphoid fevers.

8. Process for producing a bacterial vaccine according to claim 1, wherein during said extraction there is provided a vaccinating antigen fraction of molecular weight greater than 300,000.

9. Process for producing a bacterial vaccine against Salmonella fevers as in claim 1, wherein the extract of the vaccinating membrane antigens after purification and fractionality by ultrafiltration is subjected to a thorough purification by ion exchange resins.

10. Freeze-dried bacterial vaccine that can be used against Salmonella, obtained by the process of claim 9, wherein the molecular weight of the vaccinating antigen fraction is greater than 300,000.

11. A method of vaccination of humans or animals comprising administering to said humans or animals an amount sufficient to protect said humans or animals against typhoid and paratyphoid fevers of the freeze dried bacterial vaccine of claim 10 to protect said humans or animals against typhoid and paratyphoid fevers.

* * * * *